United States Patent [19]

Das

[11] 4,030,885

[45] June 21, 1977

[54] BILIRUBIN DETERMINATION

[75] Inventor: Manik L. Das, Crestwood, Mo.

[73] Assignee: Sigma Chemical Company, St. Louis, Mo.

[22] Filed: Sept. 11, 1975

[21] Appl. No.: 612,300

[52] U.S. Cl. .............................. 23/230 B; 252/408

[51] Int. Cl.[2] .............................. G01N 33/16

[58] Field of Search .................... 23/230 B; 252/408

[56] References Cited

UNITED STATES PATENTS

| | | | |
|---|---|---|---|
| 2,737,501 | 3/1956 | Sherman | 252/408 |
| 3,511,607 | 5/1970 | Green | 23/230 B |
| 3,652,222 | 3/1972 | Denney et al. | 23/230 B |
| 3,825,411 | 7/1974 | Morin | 23/230 B |
| 3,955,926 | 5/1976 | Fischer | 23/230 B |

*Primary Examiner*—Morris O. Wolk
*Assistant Examiner*—Arnold Turk
*Attorney, Agent, or Firm*—Polster and Polster

[57] ABSTRACT

An improved azobilirubin determination procedure utilizes a stable, dry lyophilized reagent. Dissolving the dry reagent in dilute hydrochloric acid produces a diazo reagent solution which is stable for several days. Cysteine hydrochloride may be added to the assay mixture to destroy excess diazo reagent, stabilize the final color, and remove interfering metal ions.

8 Claims, No Drawings

BILIRUBIN DETERMINATION

BACKGROUND OF THE INVENTION

Bilirubin is a breakdown product of the heme moiety of hemoglobin. Two forms of bilirubin have been distinguished in biological fluids. "Free" or "unconjugated" bilirubin is transported in plasma by attachment to proteins, primarily albumin. In the hepatic cells, free bilirubin is conjugated with glucuronyl or sulfate radicals to form "conjugated" bilirubin. Conjugated bilirubin is freely soluble in water, while unconjugated bilirubin is extremely insoluble in water.

Elevated levels of conjugated bilirubin are usually found in serum specimens derived from patients with obstructive jaundice; elevated levels of unconjugated bilirubin are usually found in serum specimens derived from patients with hemolytic jaundice. In the diagnosis of these disease states, both the absolute concentrations of conjugated and unconjugated bilirubin and their relative concentrations are of importance. Therefore, there is great need for simple, accurate and reproducible methods for the determination of both types of bilirubin. It may be noted that determination of only one of the types of bilirubin may be sufficient after their ratio has initially been determined for a particular patient.

Bilirubin is sold commercially both for use in standardizing procedures for determining bilirubin in biological samples and for use in research. Bilirubin determination methods are also needed in the preparation of this commercial product.

Bilirubin reacts with diazobenzene-p-sulfonic acid to form two isomeric azopigments of identical light absorption properties. Commonly, these two isomeric azopigments are collectively referred to as "azobilirubin."

Conjugated and unconjugated bilirubin differ considerably in their reaction behavior with diazobenzene-p-sulfonic acid. Conjugated bilirubin reacts directly and immediately with diazobenzene-p-sulfonic acid at an acid pH of about 1.5 to 2.0. Unconjugated bilirubin reacts with diazobenzene-p-sulfonic acid only in the presence of an accelerating agent. As a result, conjugated bilirubin is also referred to as "direct bilirubin" and unconjugated bilirubin as "indirect bilirubin."

A number of methods have been devised for the estimation of bilirubin based on the diazo reaction of bilirubin with diazobenzene-p-sulfonic acid. In these methods direct bilirubin is determined in the absence of an accelerating agent, and total bilirubin (i.e., the sum of direct and indirect bilirubin) is determined in the presence of an accelerating agent. These methods differ from each other in a number of details. Various accelerating agents have been employed, such as methanol, acetic acid, urea or a caffeine-sodium benzoate-sodium acetate reagent. Also, the pH of the ultimate reaction mixture has been varied. Azobilirubin is blue in strong acid or alkaline medium, and pink or red in neutral medium. One widely used procedure (Malloy and Evelyn, J. Bio. Chem. 119, pages 481–490 (1937), determines the pink color of azobilirubin in a neutral ultimate reaction mixture. Numerous modifications of this method have also been used. Other methods (such as Jendrassik and Grof, Biochemische Zeitschrift, 297, pages 81–89 (1938) measure the blue color of azobilirubin in alkaline medium. The alkaline azobilirubin methods have certain advantages: they are more sensitive because of the intensity of the blue azobilirubin color; they avoid protein precipitation and turbidity in the ultimate reaction mixture; and they are free from interference by hemoglobin and other colored substances usually found in biological fluids.

In the estimation of bilirubin by the alkaline azo method, it is customary to add ascorbic acid to the reaction mixture at a certain time after the addition of diazo reagent. Added ascorbic acid in the reaction mixture destroys unreacted diazobenzene-p-sulfonic acid in the reaction mixture, thereby preventing secondary reactions with indirect bilirubin in the "direct bilirubin" reaction mixture when alkali is added. In both the "direct bilirubin" and "total bilirubin" reactions, it also stabilizes the blue color of azobilirubin in the ultimate alkaline reaction mixture.

Although bilirubin has been determined by a diazo reaction for over fifty years, all of the azo methods have certain drawbacks. One of the chief drawbacks is the instability of reagents utilized in the reaction. The diazo reagent, comprising diazobenzene-p-sulfonic acid in an acidic solution, was long considered stable only for a matter of minutes, although more recently it has been reported that the reagent is essentially stable for twenty-four hours. The procedure for the preparation of fresh diazo reagent is to mix an aliquot of an aqueous solution of sodium nitrite with an aliquot of an acidic solution of sulfanilic acid. These solutions are also considered to have limited stability in storage.

To simplify the preparation of diazobenzene-p-sulfonic acid without using solutions of sulfanilic acid and sodium nitrite, Sherman and Zak, Am. J. Clin. Pathol., 23 946 (1953) introduced a diazo tablet which consisted of one hundred milligrams of sodium sulfanilate and twenty milligrams of sodium nitrite. Prior to running the diazo reaction, they dissolved this tablet in an aliquot of hydrochloric acid of know concentration to obtain the diazo solution. This has a number of problems. When the tablet is dissolved in hydrochloric acid, the sodium nitrite dissolves quickly to form nitrous acid, much of which decomposes before it can react completely with the essentially insoluble sulfanilic acid. The inhomogeneity of the tablet also contributes to variations in the final concentration of diazo compound formed from the tablet. The diazo solution derived from the diazo tablet is sometimes yellow and not suitable for use in the diazo reaction, and the shelf life of the diazo tablet is not well established.

To avoid the problems caused by the instability of diazobenzene-p-sulfonic acid and of the reagents used to prepare it, more stable diazo reagents have been prepared from various aromatic amines. The light absorption properties of isomeric azobilirubins derived from these diazo reagents have not yet been established, however. More importantly, by use of these diazo reagents it has not been possible to estimate direct bilirubin accurately and reproducibly, or in a manner which correlates well with the results obtained with diazobenzene-p-sulfonic acid.

Solutions of ascorbic acid are also known to be highly unstable. Therefore, the use of a freshly prepared solution of ascorbic acid has been recommended in the alkaline azo method of determining bilirubin. The ascorbic acid is also rapidly destroyed in the strongly alkaline ultimate solution, and therefore does not offer long-lasting protection of the blue azobilirubin color.

Summaries of various azobilirubin determinations are set out in R. J. Henry, Clinical Chemistry: Principles and Technics (Hoeber Medical Division, 1964), pages 572–594; S. R. Gambino and J. Di Re, Bilirubin Assay (American Society of Clinical Pathologists, 1968); and Denney et al U.S. Pat. No. 3,652,222 (1972), all of which are hereby incorporated by reference.

SUMMARY OF THE INVENTION

One of the objects of this invention is to provide an azo method for determining direct and total bilirubin which is simple and reliable.

Another object is to provide reagents for such a method which are far more stable than reagents known heretofore.

Other objects will become apparent in light of the following description.

In accordance with this invention, generally stated, an improved bilirubin determination method is provided which utilizes at least one improved, highly stable reagent. The improved method is preferably an alkaline azo method in which an improved diazo reagent is added to biological fluid (with or without an accelerating agent), and an improved reagent is thereafter added to destroy excess diazo reagent. The solution is then made alkaline to form a blue azobilirubin color proportional to the bilirubin concentration (total and direct) in the biological fluid.

The improved diazo reagent is made by suspending sulfanilic acid in water, adding alkali, then adding nitrite. Aliquots of this mixture are lyophilized under alkaline conditions. Preferably, the sulfanilate to nitrite ratio is approximately 28:1, although lower ratios (such as 20:1) and ratios several times as high are also usable. The lyophilized diazo reagent remains stable in storage at room temperature for indefinite periods and readily dissolves in dilute hydrochloric acid solution to form a diazo reagent solution. The diazo reagent solution formed from this dry reagent retains its full activity even after storage at 0°–5° C. for several weeks.

The improved diazo reagent is also usable in colorimetric procedures for determining other compounds, such as tyrosine, histidine, carboxyimidazole and numerous other compounds. Its value is therefore not limited to the bilirubin determination described herein.

The improved method is also simplified by substituting a sulfhydryl compound for ascorbic acid in stopping the diazo reaction with bilirubin. In the preferred embodiment, the sulfhydryl compound is cysteine hydrochloride. Unlike ascorbic acid, the cysteine hydrochloride solution is stable in storage at room temperature. Moreover, the cysteine hydrochloride reagent not only destroys excess diazo reagent as well as ascorbic acid, but also assures greater reliability in the estimation of bilirubin because it is stable in alkaline medium and because it forms complexes with certain metal ions (cupric and ferric ions) that are known to interfere with the measurement of the blue alkaline azobilirubin color.

DESCRIPTION OF THE PREFERRED EMBODIMENT

The following Examples illustrate the preferred embodiments of the various aspects of the present invention.

EXAMPLE 1

Preparation of Dry Diazo Reagent kk

A sulfanilate solution is prepared by suspending 15.0 grams of sulfanilic acid in about 400 ml. of distilled water. To the well-stirred suspension is added slowly 90 ml. of 1 N sodium hydroxide. The volume of the clear solution is made up to 1000 ml. with deionized or distilled water.

A nitrite solution is prepared by dissolving 3.5 grams of sodium nitrite in 1000 ml. of distilled or deionized water.

An alkaline diazo reagent solution is prepared by mixing 1000 ml. of sulfanilate solution with 150 ml. of nitrite solution.

Aliquots (1.0 ml.) of the alkaline diazo reagent solution are placed in glass vials, which are placed in a standard lyophilizer where the alkaline diazo reagent solution is freeze-dried, and the vials are capped under vacuum.

EXAMPLE 2

Reagent Kit

The following reagents are individually packaged in glass vials and the vials are packaged in a cardboard box as a reagent kit. All of the reagents are stable at room temperature and therefore make an easily transported and stored reagent kit for the simple and reliable determination of direct and total bilirubin. The kit supplies sufficient reagents for one hundred determinations of both direct and total bilirubin.

A. Diazo Reagent

Each of twenty vials of the dry lyophilized diazo reagent as prepared in accordance with Example 1 contains 13 mg. of sulfanilate (expressed as sulfanilic acid) and 0.457 mg. of sodium nitrite. The reagent contains twenty-eight parts by weight of sulfanilate (expressed as sulfanilic acid) per part of nitrite (expressed as sodium nitrite). The reagent is stable indefinitely at room temperature. After storage of the dry reagent for seven months at 37° C., it was reconstituted and used in the bilirubin procedure described below; the reconstituted reagent gave results which were the same (within the about plus or minus five percent error inherent in the system) as the results given by a dry reagent stored a similar time at room temperature and a freshly prepared dry reagent. Measurements were made both on a bilirubin standard in human serum albumin and on a control serum.

B. Hydrochloric Acid Reagent

A glass bottle of hydrochloric acid contains 200 ml. of 0.05 N hydrochloric acid.

C. Caffeine Reagent

An accelerating agent in a glass bottle includes 100 ml. of a solution containing 25 g./liter of caffeine and 38 g./liter of sodium benzoate in sodium acetate solution. The solution has a pH of about 8.

D. Cysteine Reagent

A diazo-destroying reagent stored in a glass vial contains 100 mg. of dry cysteine hydrochloride. The reagent is stable indefinitely.

E. Alkaline Tartrate Reagent

An alkaline buffer in a tightly capped glass bottle contains 300 ml. of solution of sodium potassium tartrate (350 g./liter) in 2.5 N sodium hydroxide. The pH of the solution is over 14.

EXAMPLE 3

Reconstitution of Dry Reagents

A'. Diazo Solution

The Diazo Reagent (Reagent A) is reconstituted by adding to its vial 6 ml. of the Hydrochloric Acid Reagent (Reagent B). The dry Diazo Reagent dissolves immediately and completely to form a colorless solution of diazotized sulfanilic acid, the concentration of which is accurately replicated whenever a vial of the dry reagent is reconstituted. The Diazo Solution has been found to be stable for up to several weeks when stored in the refrigerator at 0°–5° C.; storage of the Diazo Solution for several weeks produces no change (within the experimental error) of the color produced when a bilirubin determination is carried out as described below.

D'. Cysteine Solution

The dry Cysteine Reagent (Reagent D) is reconstituted with 10 ml. distilled water added to the vial of dry Cysteine Reagent and shaking the vial until the cysteine is dissolved. The Cysteine Solution is stable for at least three months when stored at room temperature in the dark.

EXAMPLE 4

Colorimetric Determination of Direct and Indirect Bilirubin By Alkaline Azo Method The following procedure is based on the method of Jendrassik and Grof. Serum blanks are unnecessary in this procedure unless the samples being analyzed are markedly turbid.

Two test tubes are labeled TOTAL and DIRECT. Of course, if only one type of bilirubin is being determined, only a single tube is needed. To each tube are added the following volumes (milliliters) of the named components:

| Component | TOTAL Tube (ml) | DIRECT Tube (ml) |
|---|---|---|
| Serum (or other body fluid) | 0.2 | 0.2 |
| Hydrochloric Acid Reagent (Reagent B) | — | 0.9 |
| Caffeine Reagent (Reagent C) | 0.9 | — |
| Diazo Solution (Reagent A') | 0.5 | 0.5 |

The contents of each tube are mixed well and allowed to stand for two to five minutes at room temperature. To each tube is then added 0.1 ml. Cysteine Solution (Reagent D') and the contents of each tube mixed well. To each tube is then added 1.5 ml. Alkaline Tartrate Reagent (Reagent E) and the contents are again mixed well. The sample solution (assay mixture) is then transformed to a suitable cuvet for determination of the blue azobilirubin color at 600 nm. If a narrow-bandwidth spectrophotometer (8 nm or less) is used with a 1 cm. light path cuvet, the absorbence read against water for each of the TOTAL and DIRECT sample solutions may be multiplied by a factor of 12.8 to yield bilirubin concentration in milligrams per 100 milliliters. If a wide-bandwidth spectrophotometer is used, bilirubin concentration must be read from a calibration curve prepared for that instrument either from a bilirubin standard prepared by adding bilirubin to serum, or from available serum preparations with established bilirubin values.

EXAMPLE 5

Specific Performance Characteristics of the Method

Reproducibility studies were performed by replicate assays on each of four serum pools, having mean bilirubin levels of 2.1, 6.5, 10.6 and 21.0 mg./100 ml. Standard deviations were 0.08, 0.13, 0.14 and 0.47 mg./100 ml., and coefficients of variation were 3.9, 1.9, 1.3 and 2.3 percent, respectively.

Recovery studies were conducted by increasing the bilirubin concentration of each of three aliquots of a serum pool, having a mean bilirubin value of 6.6 mg./100 ml., to levels of 6.9, 8.8 and 13.8 mg./100 ml. Multiple assays of these fortified pools revealed respective recoveries of 100, 101 and 104 percent.

Numerous variations, within the scope of the appended claims, will occur to those skilled in the art in light of the foregoing disclosure. As one example, other stable, water soluble sulfhydryl compounds having a redox potential similar to cysteine hydrochloride (such as reduced glutathione, mercaptoethanol, and other cysteine salts) may serve as reagents for destroying excess diazo reagent.

I claim:

1. In a method for colorimetrically determining bilirubin in a sample solution wherein the color of the azobilirubin formed from the coupling reaction of diazo reagent with bilirubin is measured, the improvement comprising adding a sulfhydryl compound to the sample solution after the azobilirubin has formed therein.

2. The improvement of claim 1 in which the diazo reagent is formed by acidifying a dry, lyophilized alkaline mixture of sulfanilate and nitrite.

3. The improvement of claim 1 wherein the sulfhydryl compound is cysteine hydrochloride.

4. The improvement of claim 3 wherein the method includes a step of making the assay mixture alkaline and thereafter determining the blue color of azobilirubin.

5. The improvement of claim 4 wherein the sample solution is maintained at an acid pH during the coupling reaction of direct bilirubin with the diazo reagent, the cysteine hydrochloride is added to the sample solution while the sample solution is at an acid pH, and the sample solution is thereafter made alkaline.

6. The improvement of claim 4 wherein the sample solution contains an accelerating agent and the coupling reaction is with total bilirubin.

7. In a method for determining bilirubin in a sample solution wherein the bilirubin undergoes a coupling reaction with a diazo reagent and the amount of azobilirubin formed is measured, the improvement wherein said diazo reagent is an acid solution prepared from an acid and a known quantity of a dry, lyophilized, alkaline mixture of sulfanilate and nitrite, the weight ratio of sulfanilate (expressed as sulfanilic acid) to nitrite in said dry, lyophilized alkaline mixture being at least 20:1, and wherein the sample solution is maintained at an acid pH during the coupling reaction of direct bilirubin with the diazo reagent, a sulfhydryl compound is added to the sample solution while the sample solution is at an acid pH, and the sample solution is thereafter made alkaline.

8. In a method for determining bilirubin in a sample solution wherein the bilirubin undergoes a coupling reaction with a diazo reagent and the amount of azobilirubin formed is measured, the improvement wherein said diazo reagent is an acid solution prepared from an acid and a known quantity of a dry, lyophilized, alkaline mixture of sulfanilate and nitrite, the weight ratio of sulfanilate (expressed as sulfanilic acid) to nitrite in said dry, lyophilized alkaline mixture being at least 20:1, and wherein the sample solution contains an accelerating agent and the coupling reaction is with total bilirubin, a sulfhydryl compound is added to the sample solution following the coupling reaction, and the sample solution is thereafter made alkaline.

* * * * *

UNITED STATES PATENT AND TRADEMARK OFFICE

CERTIFICATE OF CORRECTION

PATENT NO. : 4,030,885

DATED : June 21, 1977

INVENTOR(S) : Manik L. Das

It is certified that error appears in the above-identified patent and that said Letters Patent are hereby corrected as shown below:

Column 4, line 2, "Preparation of Dry Diazo Reagent kk" should be "Preparation of Dry Diazo Reagent".

Column 5, line 56, "transformed" should be "transferred".

Signed and Sealed this

*Fourth* Day of *October 1977*

[SEAL]

*Attest:*

RUTH C. MASON
*Attesting Officer*

LUTRELLE F. PARKER
*Acting Commissioner of Patents and Trademarks*